United States Patent [19]

Lissot et al.

[11] Patent Number: 4,796,197
[45] Date of Patent: Jan. 3, 1989

[54] AUTOMATED APPARATUS FOR CARRYING OUT BIOLOGICAL, BIOCHEMICAL OR PHYSICOCHEMICAL DETERMINATIONS

[75] Inventors: Jean Lissot, Brie-Comte-Robert; Jean-Pierre Vasseur, Longjumeau; Jean-Pierre Thomas, Vitry s/Seine; Claude Pascal, Combs La Ville, all of France

[73] Assignee: Rhone-Poulenc S.A., Courbevoie, France

[21] Appl. No.: 855,341

[22] Filed: Apr. 24, 1986

Related U.S. Application Data

[63] Continuation-in-part of Ser. No. 464,888, Feb. 8, 1983, abandoned.

[30] Foreign Application Priority Data

Feb. 9, 1982 [FR] France ............................... 82 02058

[51] Int. Cl.$^4$ ........................................ G01N 35/04
[52] U.S. Cl. ................................. 364/500; 422/64; 422/67; 436/47; 364/497
[58] Field of Search ............................. 364/497–500; 422/64, 65, 67, 100; 436/47

[56] References Cited

U.S. PATENT DOCUMENTS

| | | | |
|---|---|---|---|
| 3,728,080 | 4/1973 | Moran | 364/499 |
| 3,883,305 | 5/1975 | Hoskins et al. | 422/65 |
| 3,951,604 | 4/1976 | Smith et al. | 364/499 |
| 4,313,735 | 2/1982 | Yamashita et al. | 422/65 |
| 4,451,433 | 5/1984 | Yamashita et al. | 422/64 |
| 4,459,265 | 7/1984 | Berglund | 364/499 |
| 4,472,505 | 9/1984 | Manube et al. | 422/65 |
| 4,483,927 | 11/1984 | Takekawa | 436/47 |

*Primary Examiner*—Gary V. Harkcom
*Assistant Examiner*—H. R. Herndon
*Attorney, Agent, or Firm*—Stevens, Davis, Miller & Mosher

[57] ABSTRACT

Automated apparatus for carrying out biological, biochemical or physicochemical determinations, which consists essentially of an automatic machine for the preparation of solutions intended for these determinations, and of a measuring apparatus, these being connected to a single computer. This apparatus is intended in particular for the determination of antibiotics by turbidimetry.

3 Claims, 9 Drawing Sheets

AUTOMATED APPARATUS FOR CARRYING OUT BIOLOGICAL, BIOCHEMICAL OR PHYSICOCHEMICAL DETERMINATIONS

This application is a continuation-in-part of U.S. application Ser. No. 464,888 filed Feb. 8, 1983 now abandoned.

The present invention relates to an automated apparatus making it possible to carry out biological, biochemical or physicochemical determinations, and more particularly microbiological determinations, by the turbidimetric method.

An antibiotic possesses an inhibitory action against living microorganisms, and this property can be utilised for its detection and determination during the various stages of its manufacture and use.

The methods conventionally used for microbiological determinations are the so-called "dilution" method, and the diffusion method and the turbidimetric method.

The "dilution" method, although imprecise, is sufficient to determine a spectrum of action or the sensitivity of a germ to a particular antibiotic. Solutions have been provided which enable this method to be used commonly and rapidly in hospitals or medical analysis laboratories.

The diffusion method, by its very principle, is difficult to automate. This method consists in placing solutions of antibiotics, whose concentrations increase in a common ratio of 1.5 or 2, on the surface of plates carrying inoculated agar nutrient medium, generally in Petri dishes. After incubation, circular inhibition zones appear, the diameter of which bears a linear relationship to the logarithm of the concentrations. The determination is carried out by comparing the results obtained for the sample with those obtained for the standard.

The turbidimetric method consists in preparing series of solutions of antibiotics or growth factors, whose concentrations increase in a given common ratio, in a nutrient medium inoculated by the appropriate microorganism, and, after a given incubation time at a constant temperature, in evaluating the turbidity produced by all the microbial substances.

The change in turbidity is inversely proportional to the concentration of antibiotic. The turbidity measurements result in an S-curve which does not correspond to a simple mathematical formula, but makes it possible quantatively to define the activity of an antibiotic to compare the activity of an antibiotic with that of a standard.

The method of turbidimetric determination involves carrying out 3 automated or non-automated stages, on a so-called "determination unit" which consists of a given number of samples in respective test tubes. The three stages can be summarised in the following way:

(a) preparation, in the test-tubes of the determination units, of a constant volume (e.g. 1 cc) of solutions of the sample to be studied and the reference product, in concentrations which increase in a common ratio varying according to the type of antibiotic (generally from 1.1 to 1.5), and addition, to each tube, of a constant volume of inoculated nutrient medium (e.g. 9 cc), (b) incubation of the tubes in thermostatically controlled baths, the temperature of which is generally set at 37° C., and (c) photometric measurement, at the appropriate wavelength, of the turbidity after an intermediate stage involving transfer of all or part of the samples into the photometer cell or cells.

The apparatuses currently in existence lack flexibility and are only suitable for certain very precise cases. Furthermore, they are only partially automated.

It is an object of the present invention to provide an improved apparatus.

According to the invention, there is provided apparatus for performing microbiological measurements by turbidimetry, such apparatus including:

(a) means to store product solution and/or standard solution to be measured and diluent solution, (b) preparation apparatus for the preparation in test tubes of a plurality of solutions for performing the measurements, such plurality of solutions together comprising a determination unit, such preparation apparatus comprising in combination, a plurality of diluters, a transposer and a needle selector, the diluters and needle selector being controlled so as to withdraw the product solutions to be measured and/or standard solutions from said means to store and place same in test tubes in volumes which increase at a predetermined ratio, to make up the solutions in the test tubes by adding diluent and withdraw and distribute a given volume of liquid nutrient in the test tubes, the transposer allowing successive performance of the withdrawal and distribution in the test tubes, such distribution being a random distribution, such preparation being without manual intervention and without the transfer of liquid, (c) a dry incubator for receiving a said determination unit comprising a plurality of test tubes filled by the preparation apparatus, (d) measuring apparatus for determining the turbidity of the samples in the test tubes after incubation, (e) a single computer effective to control the preparation apparatus, the incubator and the measuring apparatus, to memorize the conditions of preparation, to generate the random distribution, and to acquire and statistically interpret and present the results.

Using such an apparatus, according to the teachings of the present invention, it is possible to reduce the causes of errors by eliminating the handling operations in particular and by treating the various solutions of the sample and the reference product simultaneously in a single operation, thus controlling the synchronism of the microbial culture in the determination unit.

By using for example an apparatus according to the invention for microbiological determinations by turbidimetry, it is possible directly to compare the activity of a sample with that of a standard product or to determine the activity of an antibiotic by evaluating the concentration which reduces the growth of the micro-organism by 50%. A determination unit consists for example of 24 tubes and remains unalterable from the preparation stage to the photometric measurement stage.

If the apparatus of the invention is used to monitor a sample, i.e. to compare the activity of a sample with that of a standard product, it is necessary to distribute the following in the tubes of the determination unit:

a range of for example four concentrations of the sample in a suitably chosen common ratio (1.1 to 1.5), starting from a single solution, and a range of for example four concentrations of the standard product in an identical common ratio, and, in order to reduce the causes of errors, in particular those due to the random nature of microbial multiplication, to repeat each concentration range a certain number of times, for example 3 times, the tubes being arranged randomly so as to permit subsequent statistical analysis of the results.

Each solution is prepared with a constant volume by adding a given amount of diluent, for example distilled water, to each sample so that each tube contains the same volume of solution (e.g. 0.3 cc).

Finally, each tube is made up by adding the same volume of inoculated nutrient liquid (e.g. 2.7 cc).

If the apparatus is used to determine the strength of a sample of unknown activity, it is necessary to prepare a wider concentration range in the determination unit such as:

one range of seven concentrations with a control not containing antibiotic, it being possible for each concentration range to be repeated three times.

However, as precision is not necessarily sought in this case, it is not obligatory to repeat each concentration, in which case it is possible to determine the activity of three different products simultaneously for the same number of samples in the determination unit.

According to the invention, the determination unit can be prepared automatically with the aid of an automatic machine which consists of a combination of eight diluters and a transposer.

The automatic preparation machine must perform the following functions:

withdrawal, from a supply thereof, of volumes of a solution of the antibiotic being investigated, the volumes increasing in a suitably chosen common ratio, and placing same in test tubes of the determination unit, withdrawal from a supply thereof of an additional given volume of diluent and placing in test tubes such that for example the total volume of the solution of antibiotic and the diluent is 0.3 cc, removal of a given volume, e.g. 2.7 cc, of inoculated nutrient medium kept at a temperature of the order of +4° C., and placing in test tubes, randomisation of the distribution, and storage of all the above data.

All the removal and distribution functions are performed by eight diluters and the other functions are performed by a transposer, which also includes a needle selector for placing the needles in the appropriate positions.

In order that the present invention may more readily be understood, the following description is given, merely by way of Example, reference being made to the accompanying drawings, in which.

Figure 1:
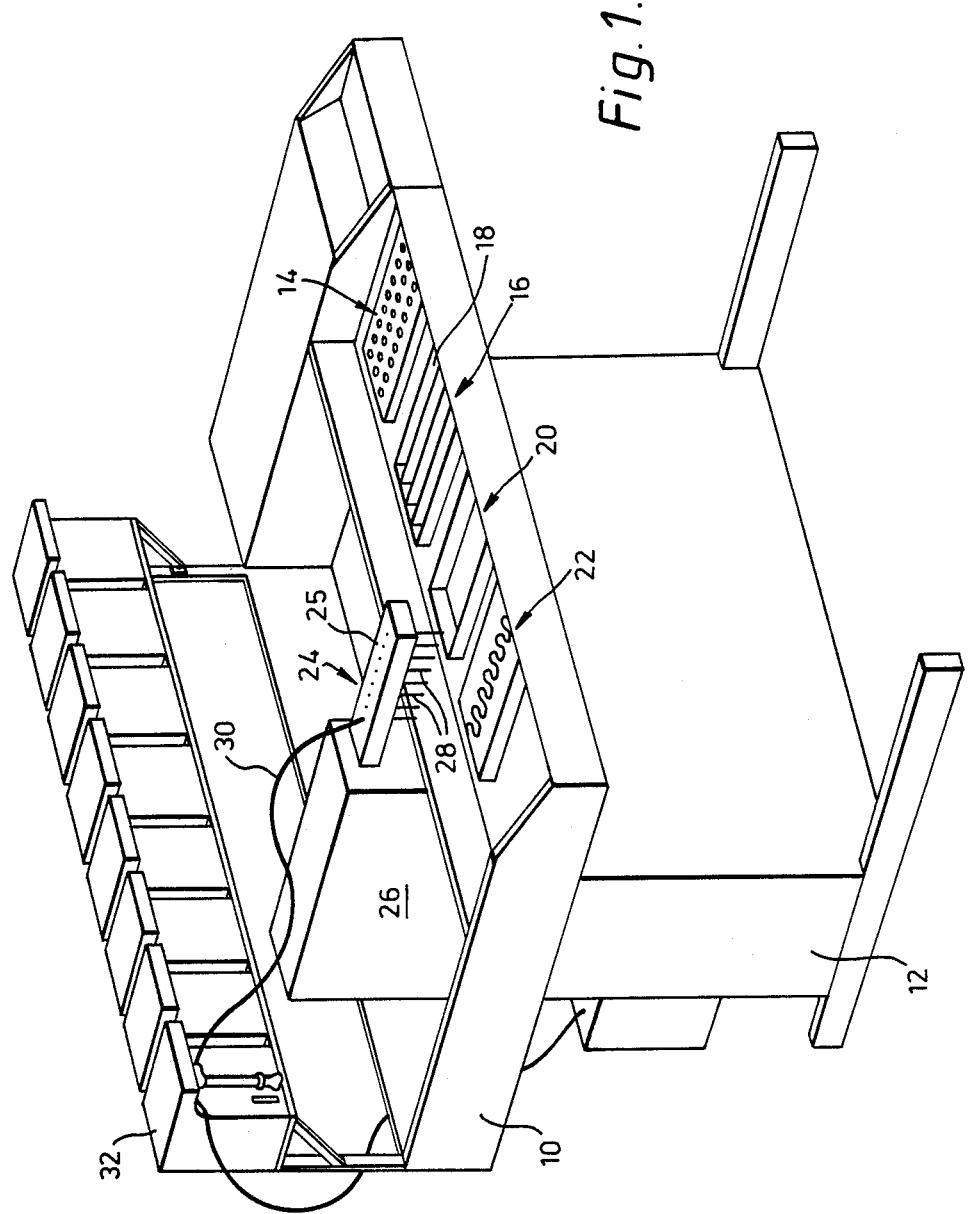
FIG. 1 is a perspective view of one embodiment of apparatus according to the present invention.

Referring first to FIG. 1, the apparatus illustrated includes a generally horizontal table 10 mounted on a support frame 12, the table 10 including, starting from the right hand side, a rack 14 for mounting twenty four test tubes, a section 16 including four troughs 18, a washing station 20 and a needle wiping station 22.

The apparatus illustrated includes only a single station but it is contemplated that one could have two symmetrical working stations, one on the right as shown, and one on the left, near the needle washing-/wiping station and, like the first station, comprising a section with four troughs and a rack containing twenty-four tubes.

Above the table 10 of the preparation machine there is a selector 24 including a needle support head 25, which is fixed to a carriage 26, which can be moved in a horizontal plane and in a vertical plane by means of two step-wise motors controlled by a microprocessor. The head carries eight needles 28 each of which is fixed to an electromagnet (not shown) controlled by the microprocessor. The eight needles 28 are located in a vertical plane parallel to the axis of the troughs 18 located in the section 16 and these needles are each connected by a line 30 to a diluter 32 to be described below. The needles 28 are normally in a lowered position, in which they can remove antibiotic or diluent from a trough 18. The energizing of one of the electromagnets causes it to raise its associated needle by a height of about 10 mm. In the raised position, this needle no longer dips into the trough 18 containing the solution of antibiotic or diluent. This procedure avoids any unnecessary inaccurate withdrawal, internal contamination by diffusion or external contamination by passing from one solution of the antibiotic to another.

Figure 2:
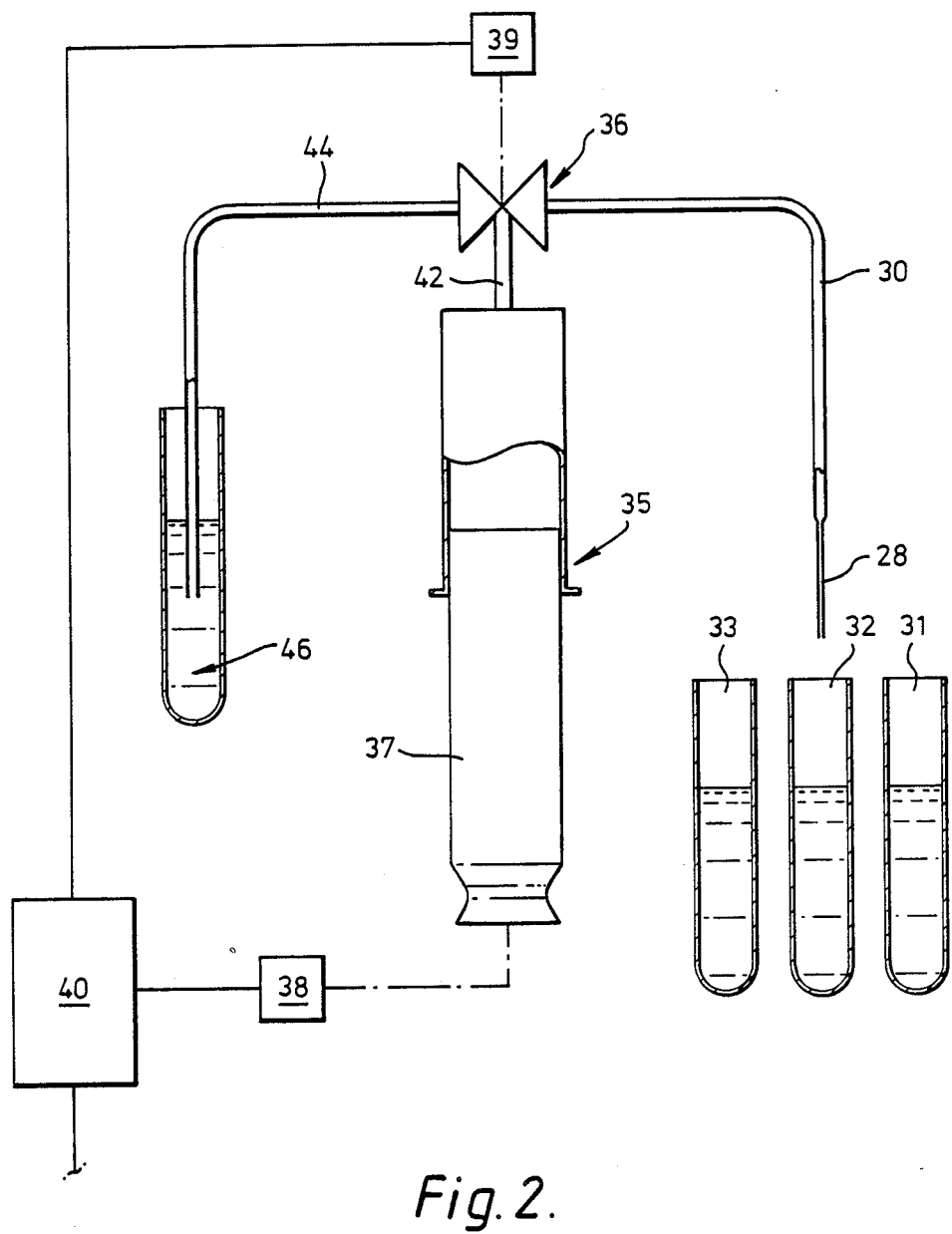
FIG. 2 is a schematic diagram of the diluter used in the apparatus of FIG. 1.

Randomization, i.e. the random distribution, of the various solutions in the tubes 31, 32, 33 (FIG. 2) is calculated and stored by the microprocessor, which will re-establish the coherent order of the product and of the concentrations before analysis of the results by statistical calculation.

Each diluter (FIG. 2) comprises a pump consisting of an accurate 5 cc syringe 35 and the upper end of which is connected to a three way valve 36 having two operating positions. Movement of the piston 37 of the syringe 35 is controlled by a motor 38 while the movement of the valve 36 is controlled by a motor 39. Operation of the motors 38 and 39 is effected by a microprocessor, in this case shown schematically at 40.

The valve is connected firstly via line 42 to the syringe 35, secondly via line 44 to a source 46 (see also FIG. 1) of nutrient, the temperature of which is kept at a value of about +4° C., and to the tube 30 connected to each needle 28.

In use of the diluter, with the tube 44 full of nutrient liquid, the successive removals of solution of antibiotic and diluent are carried out. After the valve has been switched over, a constant volume of nutrient medium is removed. After repositioning of the valve, the total amount removed is delivered into the test tube of the determination unit.

To prevent mixing by diffusion during the successive removals, an air bubble having a volume of 5 to 10µl is introduced, in order to separate one removed amount from the next. Furthermore, an air bubble is introduced into the end of the needle so as to eliminate the formation, at its end, of droplets which would be likely to be thrown off during the movements of the needle support head.

Each diluter is independent and is controlled separately by the microcomputer 40.

Table I shows, by way of example, a control diagram of the various members of the automatic preparation machine.

TABLE I

| Instruction No. | Transposer | Diluters | Needle-selecting electromagnet |
|---|---|---|---|
| 10 | Reset to zero | | |
| 20 | Wiping of the needles | | |
| 30 | | Removal of an air bubble from all the diluters | |
| 40 | Horizontal movement of the needle support head above the "standard" trough | | |
| 50 | | | Excitation: selection of needles in the high position (needles for removing sample) |
| 60 | Vertical descending movement of the needle support head | | |
| 70 | | Removals of the standard by the selected diluters | |
| 80 | Vertical ascending movement of the needle support head | | |
| 90 | | | Cut-off of the excitation: needles in the low position |
| 100 | Horizontal movement of the needle support head above the "sample" trough | | |
| 110 | | | Excitation: selection of needles in the high position (needles which have removed the standard) |
| 120 | Vertical descending movement of the needle support head | | |
| 130 | | Removal of the samples by the selected diluters | |
| 140 | Vertical ascending movement of the needle support head | | |
| 150 | | | Cut-off of the excitation: all the needles in the low position |
| 160 | | Removal of an air bubble from all the diluters | |
| 170 | Horizontal movement of the needle support head above the "diluent" trough | | |
| 180 | Vertical descending movement of the needle support head | | |
| 190 | | Removal of diluent by all the diluters | |
| 200 | Vertical ascending movement of the needle support head | | |
| 210 | | Removal of an air bubble | |
| 220 | Horizontal movement of the support head above | | |

TABLE I-continued

| Instruction No. | Transposer | Diluters | Needle-selecting electromagnet |
|---|---|---|---|
| | the determination unit | | |
| 230 | | Positioning of the valve | |
| 240 | | Removal of the nutrient liquid by the diluters | |
| 250 | | Repositioning of the valve of each diluter | |
| 260 | Vertical descending movement of the needle support head | | |
| 270 | | Distribution in the test-tubes of the determination unit | |
| 280 | Vertical ascending movement of the needle support head | | |
| 290 | back to instruction No. 20 | | |

The determination unit for instance of twenty four per sample in test tubes prepared in this way is placed in an incubator equipped with a thermostatically controlled, dry heating means (the temperature of which has been set beforehand) for a predetermined time.

When the incubation is ended, the growth of the microorganism is stopped by the addition of one drop of formaldehyde. The determination unit is placed in the housing of an automatic photometer which permits direct measurement of the optical density of the solutions studied, the walls of the rack being provided, at the location of each tube, with windows transmitting the beam from the light source to the photoelectric cell.

By way of example, the photometer, which can be a commercially available apparatus, is an analyzer with twenty four individual photometric channels. The light from a xenon lamp is conducted by twenty four quartz optical fibres to the twenty four measuring cells. However, there is a distortion of the turbidimetric measurement between the twenty four light beams, and this must be corrected.

The recording of experimental values obtained for different microorganisms and different turbidity levels makes it possible to calculate a correction factor for each optical channel. All these correction factors are stored by means of a computer program.

The experimental data transferred to and corrected by the computer are analyzed according to the conventional statistical programs; the results are expressed on a printer in the form of a table and a regression curve.

More particularly, the function of the computer is:

to run the automatic preparation machine according to an instruction sequence, such as that described in Table I above, relating to the transposer, the diluters and the needle selector, to randomize the removals, to store the above functions and the identification of the determination unit, to acquire the photometric measurements, to make the corrections to these measurements and carry out statistical analysis thereof, and to edit and file the results.

Furthermore, the computer makes it possible to adapt this set of functions and programs to the chosen type of determination and to the change in the procedure for carrying out the said determination.

The determination sequence forming the subject of the present invention can be used not only for microbiological determination by turbidimetry but also for all determinations which require the preparation of solutions whose concentration varies according to an arrangement capable of randomization with or without repetition, or which require the addition of different reagents in variable and programmable proportions and which involve enzymatic, immunological, serological, chemical or biochemical reactions.

The assay sequence requires four basic stages to be carried out, these being, in chronological order:

the preparation of the solutions in the tubes, incubation, the reading of the optical densities, the calculation and interpretation of the results.

The computer performs the calculations and controls the whole sequence. It both centralizes the data and directs the apparatus.

Each stage of the analytical sequence is characterized by the operation of a module or specific program on an assay unit consisting of the carrier which is a physical assay unit and a fundamental logic unit in the data processing application.

There are four main modules:

IDE (identification): this samples all the technical information at the terminal relating to the assay performed on a given carrier.

PRE (preparation): this directs the preparation device in order to prepare a given carrier, according to the chosen type of assay (monitoring or study of new product).

PHO (photometry) linked with the photometer, this samples the opitcal densities of a given carrier which has already been prepared.

CAL (calculation): this performs the calculations and lists the results relating to the assay performed on a given carrier, which has already been identified, prepared and subjected to photometry.

These four interacting modules are activated by the terminals.

Figure 3:
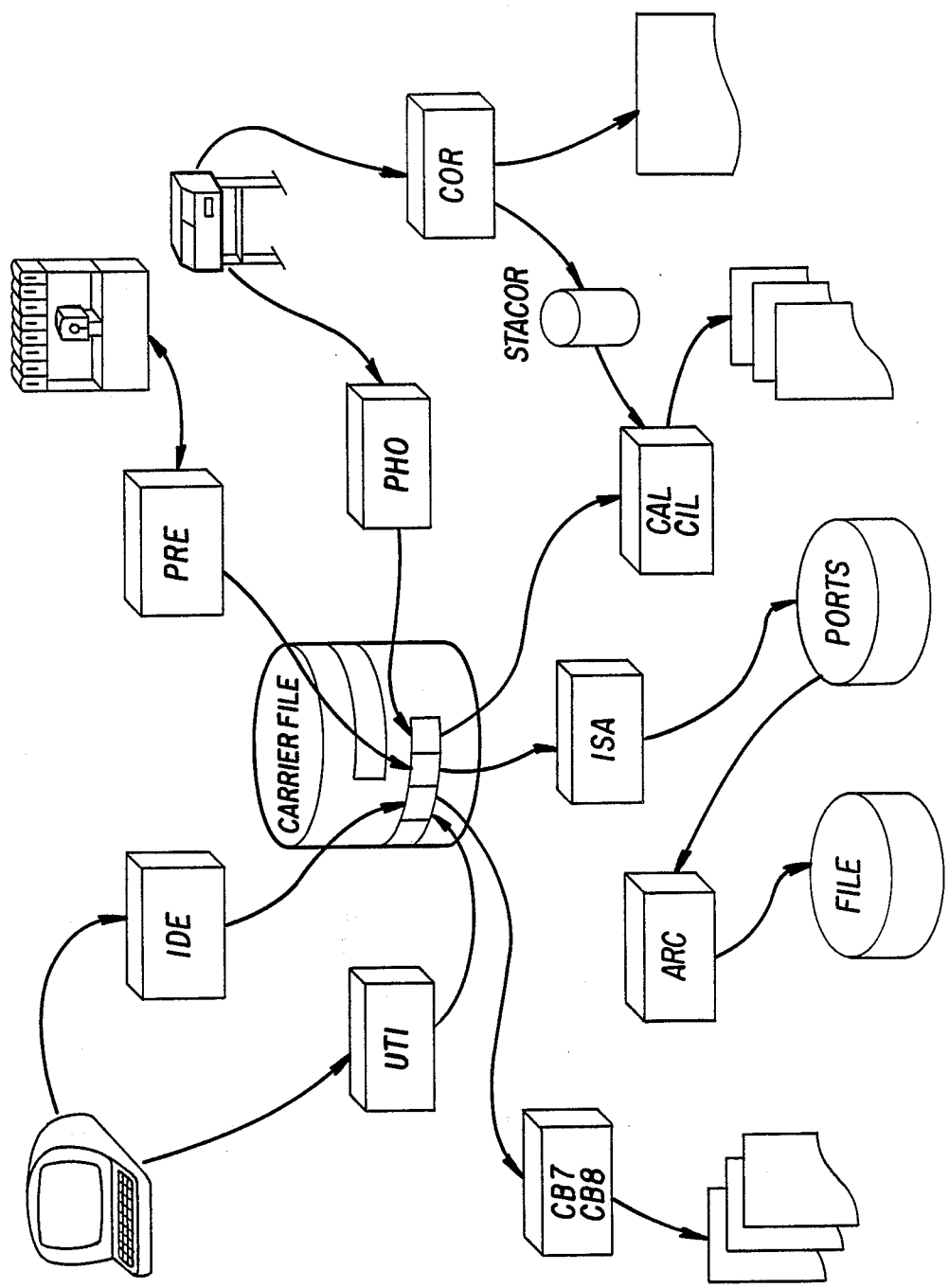
FIG. 3 is a diagram of the general organisation of the modules around the carrier file.

In order to be able to follow chronologically each carrier and centralise the data derived from the modules, it is necessary to use a central collecting file (carrier file) (see FIG. 3) which collects the data provided by each of the modules for the preparation of the dilutions and for the expression of the results, and which enables the changes in the carriers to be followed by means of suitable monitoring. Each recording in the "carrier file" contains several specific areas relating to the characteristics of the carrier, and areas assigned to the IDE, PRE and PHO modules.

The principle of the PRE module is described in Table I. The CAL module, which enables three types of analysis to be performed (control assay, test assay without reference, test assay with reference) from the optical density readings, uses calculations and calculation procedures as defined and imposed by the French Pharmacopoeia.

Figure 4:
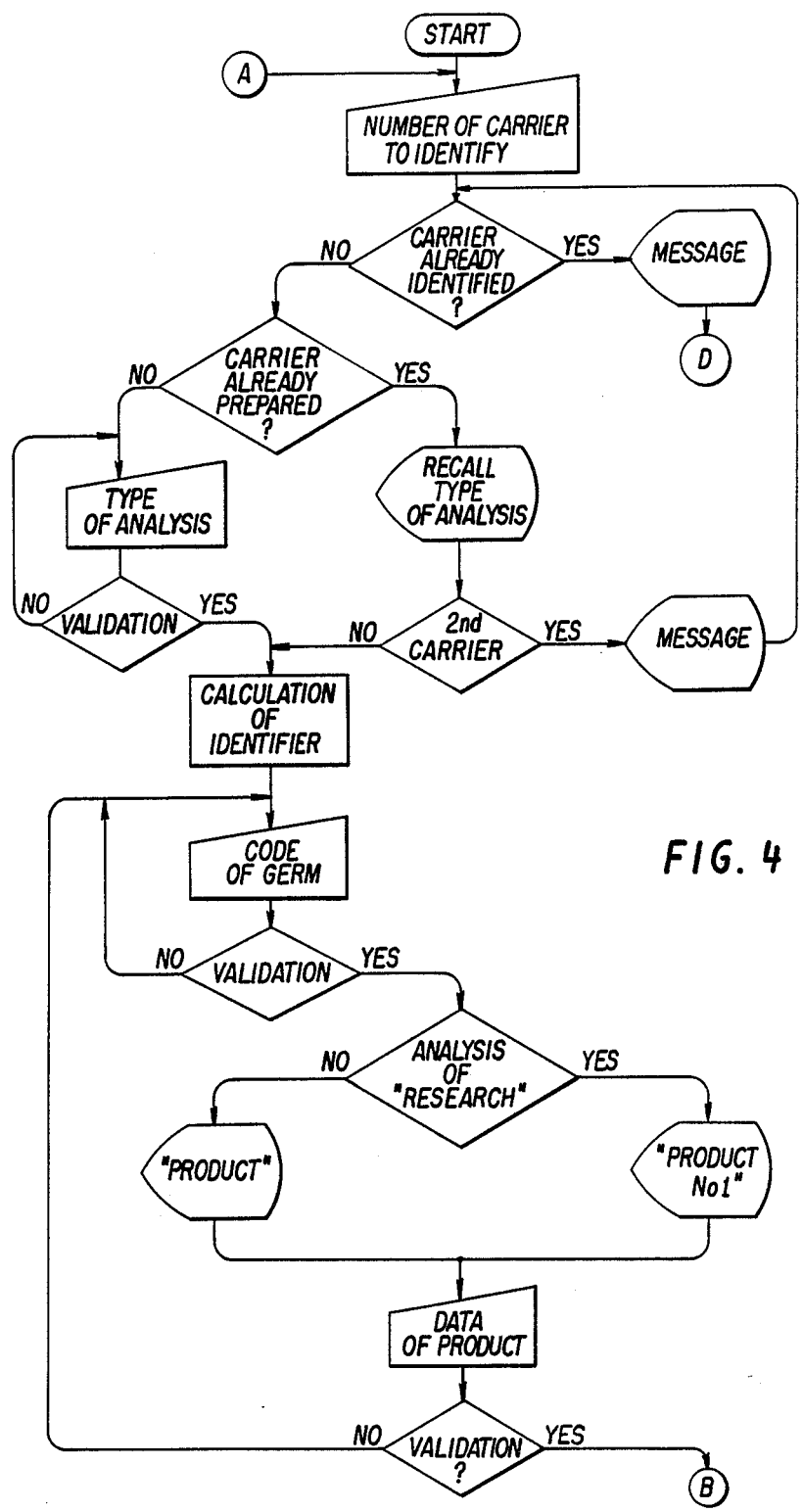
FIGS. 4, 5 and 6 show the flow chart of the IDE module.
Figure 5:
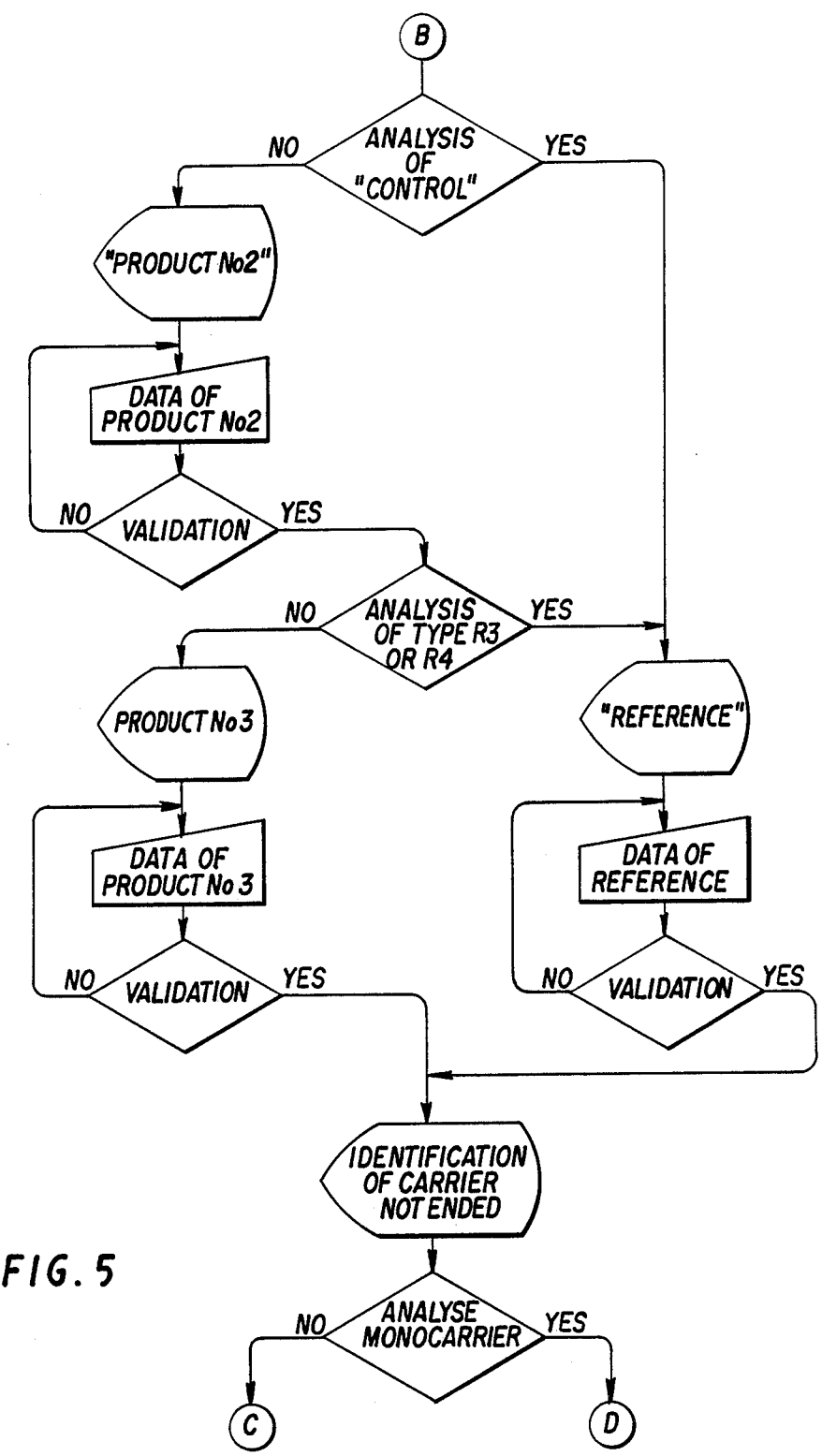
Figure 6:
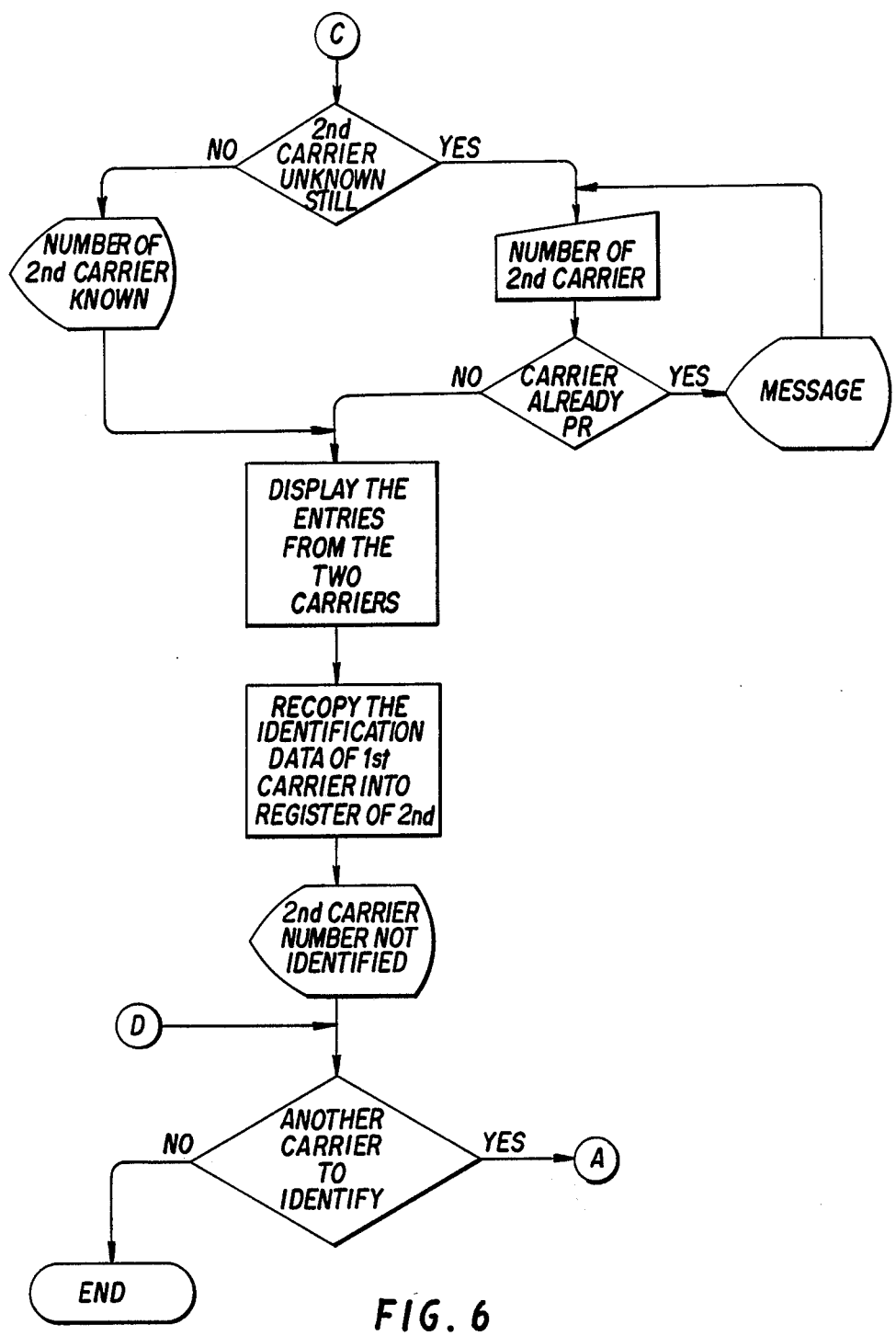

The IDE module makes it possible to gather at the keyboard of a terminal the data required for the calculation and listing of the assays performed on the carrier (characteristics of the carrier, type of analysis, characteristics of the samples and of the reference product). The flow chart of the IDE module is shown in FIGS. 4, 5 and 6.

Figure 7:
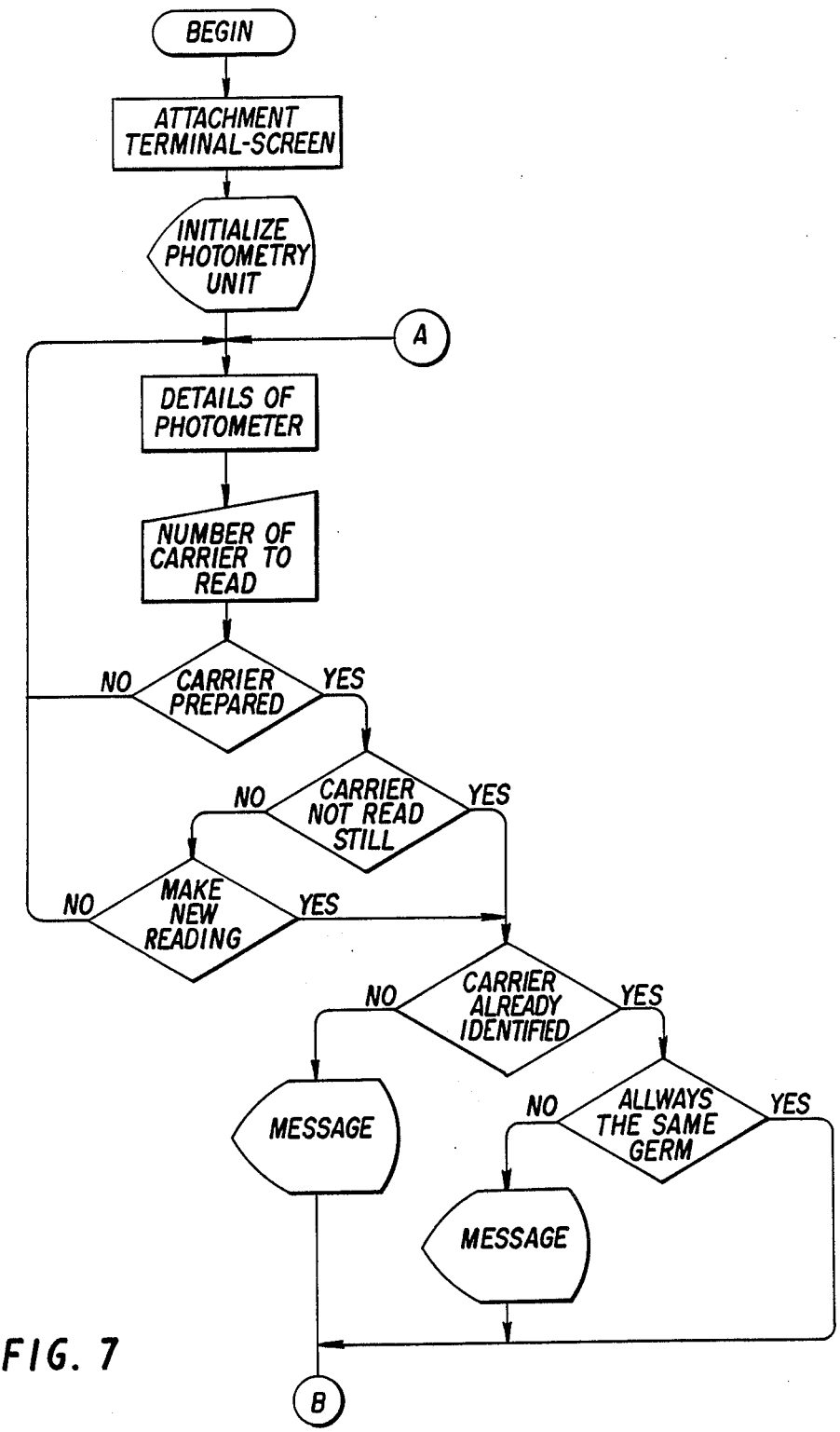
FIGS. 7, 8 and 9 show the flow chart of the PHO module.
Figure 8:
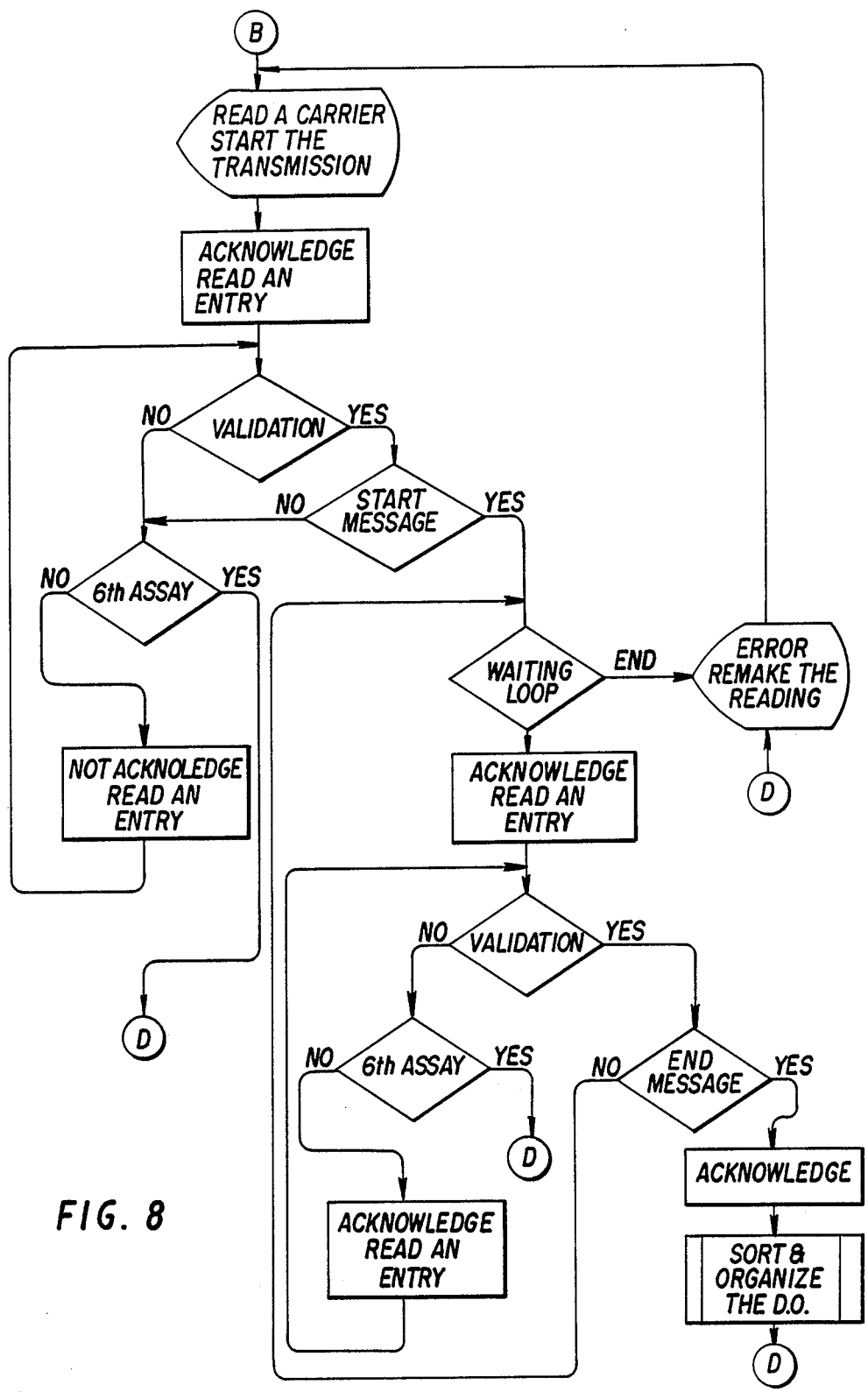
Figure 9:
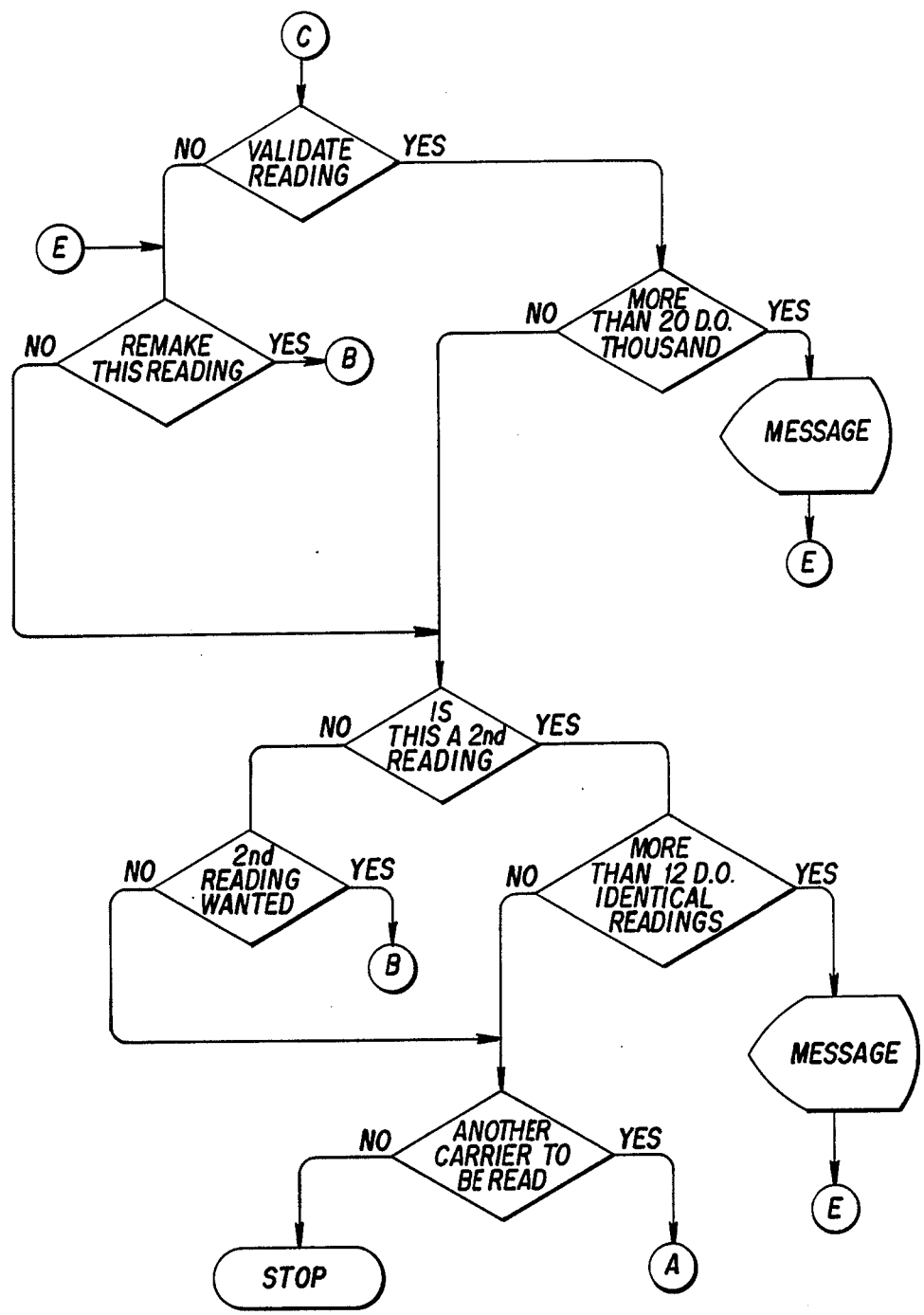

The PHO module guides the operator who performs the reading of a carrier on a photometer, sorts and edits the optical densities read, and records the data in the "carrier file". The flow chart of the PHO module is shown in FIGS. 7, 8 and 9.

We claim:

1. Apparatus for performing microbiological measurements by turbidimetry, such apparatus including:
    (a) means to store a liquid nutrient and constituents for preparing samples including diluent solution and at least one of product solution and standard solution to be measured,
    (b) preparation apparatus for the preparation in a plurality of test tubes arranged on a support of a plurality of solutions for performing the measurements, such plurality of solutions together comprising a determination unit, such preparation apparatus comprising in combination, a plurality of needles for dispensing liquid into the test tubes, a plurality of diluters each connected to a respective needle, a transposer and a needle selector, said plurality of diluters and needle selector being controlled so as to draw at least one of the product solutions to be measured and standard solutions from said means to store via selected ones of the said plurality of needles into the respective diluters, and subsequently place same in test tubes in volumes which increase at a predetermined ratio, to make up the solutions in the test tubes by drawing a volume of diluent from said means to store and adding it to said test tubes via said needles, and withdraw from said means to store a given volume of liquid nutrient and distribute it to the test tubes, the transposer allowing successive performance of the withdrawal and distribution in the test tubes, the distribution of the samples and liquid nutrient amongst the arrangement of test tubes being a random distribution, such preparation being without manual intervention and without the transfer of liquid,
    (c) a dry incubator for receiving a said determination unit comprising a plurality of test tubes filled by the preparation apparatus,
    (d) measuring apparatus for determining the turbidity of the samples in the test tubes after incubation, and
    (e) a single computer effective to control the preparation apparatus, the incubator and the measuring apparatus, to store the conditions of preparation to generate the random distribution and store the distribution of samples and liquid nutrient amongst the test tubes, and to acquire and statistically interpret measurements with respect to siad stored random distribution of samples and liquid nutrient and to present the results.

2. A method of performing microbiological measurements by turbidimetry, comprising the steps of:
    (a) storing in storing means a liquid nutrient and constituents for preparing samples including diluent solution and at least one of product solution and standard solution to be measured,
    (b) preparing in a plurality of test tubes arranged on a support a plurality of solutions for performing the measurements, such plurality of solutions together comprising a determination unit, by using a plurality of needles for dispensing liquid into the test tubes, a plurality of diluters each connected to a respective needle, a transposer and a needle selector, and controlling the plurality of diluters and needle selector so as to draw at least part of the product solutions to be measured standard solutions from said storing means via selected ones of the plurality of needles into the respective diluters, and subsequently placing same in test tubes in volumes which increase at a predetermined ratio, making up the solutions in the test tubes by drawing a volume diluent from said storage means and adding it to said test tube via said needles and withdrawing from said storage means a given volume of liquid nutrient and distributing it in the test tubes, the transposer allowing successive performance of the withdrawal and distribution in the test tubes, the distribution of the samples and liquid nutrient amongst the arrangement of test tubes being a random distribution, such preparation being without manual intervention and without the transfer of liquid,
    (c) placing said determination unit, comprising a plurality of test tubes filled by the preparation apparatus in a dry incubator, and
    (d) determining the turbidity of the samples in the test tubes after incubation,
    wherein a single computer is used to control said steps of preparation, incubation and determining the turbidity, storing the conditions of preparation, generating the random distribution, storing the distribution of samples and liquid nutrient amongst the test tubes and acquiring and statistically interpreting measurements with respect to said stored random distribution of samples and liquid nutrient and presenting the results.

3. A method of preparing mixtures, in variable and programmable proportions of at least one of different reagents and solutions for carrying out enzymatic, chemical, biochemical, immunological or servological determinations comprising the steps of:
    (a) storing in storing means a liquid nutrient and constituents for preparing samples including diluent solution and one of product solution and standard solution to be measured,
    (b) preparing in a plurality of test tubes arranged on a support a plurality of solutions for performing the measurements, such plurality of solutions together comprising a determination unit, by using a plurality of needles for dispensing liquid into the test tubes, a plurality of diluters each connected to a respective needle, a transposer and a needle selector, and controlling the plurality of diluters and needle selector so as to draw at least part of the product solutions to be measured and standard solutions from said storing means via selected ones of the plurality of needles into the respective diluters, and subsequently placing same in test tubes in volumes which increase at a predetermined ratio, making up the solutions in the test tubes by drawing a volume of diluent from said storage means and adding it to said test tubes via said needles and withdrawing from said storage means a given volume of liquid nutrient and distributing it in the test tubes, the transposer allowing successive performance of the withdrawal and distribution in the test tubes, the distribution of the samples and liquid nutrient amongst the arrangement of test tubes being a random distribution, such preparation being without manual intervention and without the transfer of liquid, (c) placing said determination unit, comprising a plurality of test tubes filled by the preparation apparatus in a dry incubator, and (d) determining the turbidity of the samples in the test tubes after incubation, wherein a single computer is used to control said steps of preparation, incubation and determining the turbidity, storing the conditions of preparation, generating the random distribution, storing the distribution of samples and liquid nutrient amongst the test tubes and acquiring and statistically interpreting measurements with respect to said stored random distribution of samples and liquid nutrient and presenting the results.

* * * * *